(12) United States Patent
Gorsuch et al.

(10) Patent No.: US 7,267,771 B2
(45) Date of Patent: *Sep. 11, 2007

(54) APPARATUS FOR THERAPEUTIC APHERESIS

(75) Inventors: Reynolds G. Gorsuch, Yountville, CA (US); Harold W. Peters, Martinez, CA (US); Harold H. Handley, Jr., Novato, CA (US); Tommy Cooper, Friendswood, TX (US)

(73) Assignee: Transvivo, Inc., Napa, CA (US)

( * ) Notice: Subject to any disclaimer, the term of this patent is extended or adjusted under 35 U.S.C. 154(b) by 367 days.

This patent is subject to a terminal disclaimer.

(21) Appl. No.: 11/009,226

(22) Filed: Dec. 10, 2004

(65) Prior Publication Data
US 2005/0155932 A1    Jul. 21, 2005

Related U.S. Application Data

(62) Division of application No. 10/219,082, filed on Aug. 13, 2002, now Pat. No. 6,849,183.

(51) Int. Cl.
*B01D 63/02* (2006.01)
*A61M 37/00* (2006.01)
*B01D 61/00* (2006.01)

(52) U.S. Cl. .......... 210/321.88; 210/321.71; 210/321.79; 210/645; 210/646; 210/650; 210/321.69; 604/5.01; 604/6.01; 604/6.09

(58) Field of Classification Search .............. None
See application file for complete search history.

(56) References Cited

U.S. PATENT DOCUMENTS

| 4,235,231 A | 11/1980 | Schindler et al. |
| 4,440,641 A | 4/1984 | Ostertag |
| 4,769,146 A | 9/1988 | Schmidt |
| 4,832,034 A | 5/1989 | Pizziconi et al. |

(Continued)

FOREIGN PATENT DOCUMENTS

EP    0321448    6/1989

(Continued)

OTHER PUBLICATIONS

A. Sueoka, Present Status of Apheresis Technologies: Part 2. Membrane Plasma Fractionator. *Therapeutic Apheresis*, vol. 1, No. 2, pp. 135-146, May 1997.

(Continued)

*Primary Examiner*—Krishnan S. Menon
(74) *Attorney, Agent, or Firm*—Knobbe Martens Olson & Bear LLP

(57) ABSTRACT

Apparatus for carrying out therapeutic apheresis includes a filter device for being implanted in a blood vessel for carrying out in-vivo plasma separation having one or more elongated hollow tubes and a plurality of elongated hollow microporous fibers capable of separating plasma from whole blood at pressure and blood flow within a patient's vein, a multiple lumen catheter secured to the proximal end of the filter device having one or more lumens in fluid communication with the interior of said one or more hollow tubes and a plasma return lumen, and therapeutic apheresis apparatus for removing and/or separating selected disease-related components from the separated plasma and means for directing plasma between said catheter and the selective component removal apparatus.

41 Claims, 4 Drawing Sheets

U.S. PATENT DOCUMENTS

| | | |
|---|---|---|
| 4,950,224 A | 8/1990 | Gorsuch et al. |
| 5,145,583 A | 9/1992 | Angleraud et al. |
| 5,151,082 A | 9/1992 | Gorsuch et al. |
| 5,152,743 A | 10/1992 | Gorsuch et al. |
| 5,224,926 A | 7/1993 | Gorsuch et al. |
| 5,284,583 A | 2/1994 | Rogut |
| 5,605,627 A | 2/1997 | Carlsen et al. |
| 5,716,689 A | 2/1998 | Rogut |
| 5,735,809 A | 4/1998 | Gorsuch |
| 5,968,004 A | 10/1999 | Gorsuch |
| 5,980,478 A | 11/1999 | Gorsuch et al. |
| 5,980,481 A | 11/1999 | Gorsuch |
| 6,013,182 A | 1/2000 | Emi et al. |
| 6,102,884 A | 8/2000 | Squitieri |
| 6,224,765 B1 | 5/2001 | Watanabe et al. |
| 6,607,501 B2 * | 8/2003 | Gorsuch ............ 604/5.01 |
| 6,659,973 B2 * | 12/2003 | Gorsuch et al. ......... 604/6.04 |
| 6,802,820 B1 | 10/2004 | Gorsuch et al. |
| 6,899,692 B2 * | 5/2005 | Gorsuch et al. ........... 604/6.09 |
| 2002/0087109 A1 * | 7/2002 | Gorsuch et al. ........... 604/6.04 |

FOREIGN PATENT DOCUMENTS

| | | |
|---|---|---|
| EP | 0341979 | 11/1989 |
| EP | 0 882 494 A1 | 12/1998 |
| FR | 2566003 | 12/1985 |
| JP | 60-232204 | 11/1985 |
| JP | 9323031 | 12/1997 |

OTHER PUBLICATIONS

Ronco, et al. A Novel approach to the Treatment of Chronic Fluid Overload with a New Plasma Separation Device, *Cardiology 2001*; 96:135-146, Jan. 2002.

Handley, et al., Intravenous Catheter for Intracorporeal Plasma Filtration, *Blood Purification 2002*, 20:61-69, Jan. 24, 2002.

* cited by examiner

APPARATUS FOR THERAPEUTIC APHERESIS

RELATED APPLICATION

This application claims priority to and is a divisional of application Ser. No. 10/219,082, now U.S. Pat. No. 6,849,183, entitled "Method and Apparatus for Therapeutic Apheresis," filed on Aug. 13, 2002, which is incorporated herein by reference in its entirety.

BACKGROUND OF THE INVENTION

In the field of medicine, the term "therapeutic apheresis" refers to techniques for treating diseases using the patient's blood. Current medical practice extracts whole blood from the patient and, as a first stage, separates the plasma from the blood ex-vivo by centrifugal or membrane separation, and in a second stage treats the separated plasma by various techniques. The treated plasma and blood are recombined ex-vivo and returned to the patient. In the simplest procedure the separated plasma including the pathogenic macromolecules is discarded and substitution fluids such as fresh frozen plasma and albumen solution are re-infused to the patient.

In all of the aforesaid and currently practiced therapeutic apheresis procedures, whole blood must be removed from the body and processed in two ex-vivo stages. However, removal and treatment of whole blood has major disadvantages. Whole blood removal results in the necessity to heparinize or anticoagulate the patient to minimize clotting in the ex-vivo circuit and apparatus. Such treatment is counter-indicated in most surgical patients and deleterious to others due to consequential damage to blood components and the removal of vital blood components unrelated to the therapy. Removing and treating whole blood ex-vivo dictates that the procedure be a "batch" or intermittent process with attendant loss of efficiency and confinement of the patient to a clinical setting where support systems and machinery are available. Removal of whole blood also exposes the patient to contamination by viral and/or bacterial infection from nosocomial sources, and removal of erythrocytes, platelets and other large cellular blood components exposes them to risk of damage due to mechanical and chemical exposure to non-biocompatible surfaces of ex-vivo apparatus.

SUMMARY OF THE INVENTION

The present invention relates to methods and apparatus for carrying out therapeutic apheresis. In the present invention, plasma, not whole blood, is removed from the patient in a first stage of therapeutic apheresis. Plasma separation is performed in-vivo by a plasma separation filter placed in an appropriate vein and the separated plasma is pumped to a therapeutic apheresis selective component removal system for separating and removing selected disease-related plasma components or plasma containing such components such as toxins, antibodies, proteins, bacteria, and/or viruses. After the appropriate disease-related plasma component is extracted by the therapeutic apheresis apparatus, the processed plasma, and if desired fresh plasma, is pumped to the patient.

In a preferred embodiment, a system used for carrying out therapeutic apheresis comprises apparatus including a filter device for being implanted in a blood vessel for in-vivo plasma separation incorporating a plurality of elongated microporous hollow fibers having an asymmetrical fiber wall morphology in which the inner wall surface along the interior fiber lumen has a lower mass density and the fiber wall adjacent to the outer wall surface has a higher mass density. A preferred filter device comprises one or more elongated hollow tubes to which opposite ends of each of the fibers are secured so that the interior of the one or more hollow tubes communicates with the interior of each of the elongated hollow fibers. The system includes a triple lumen catheter, secured to a proximal end of the one or more hollow tubes for directing blood plasma passing through the fiber walls and into the fiber lumen to therapeutic apheresis selective component removal apparatus. The system also includes fluid control piping and cooperating pumps for directing plasma between system components. The system includes backflush components comprising piping, backflush pump and source of backflush fluid selectively directed to the filter device for a duration and flow rate sufficient to substantially cleanse filter pores. In a preferred embodiment, operation of the system is controlled by a microprocessor/controller.

DETAILED DESCRIPTION OF THE PREFERRED EMBODIMENTS

Figure 1:
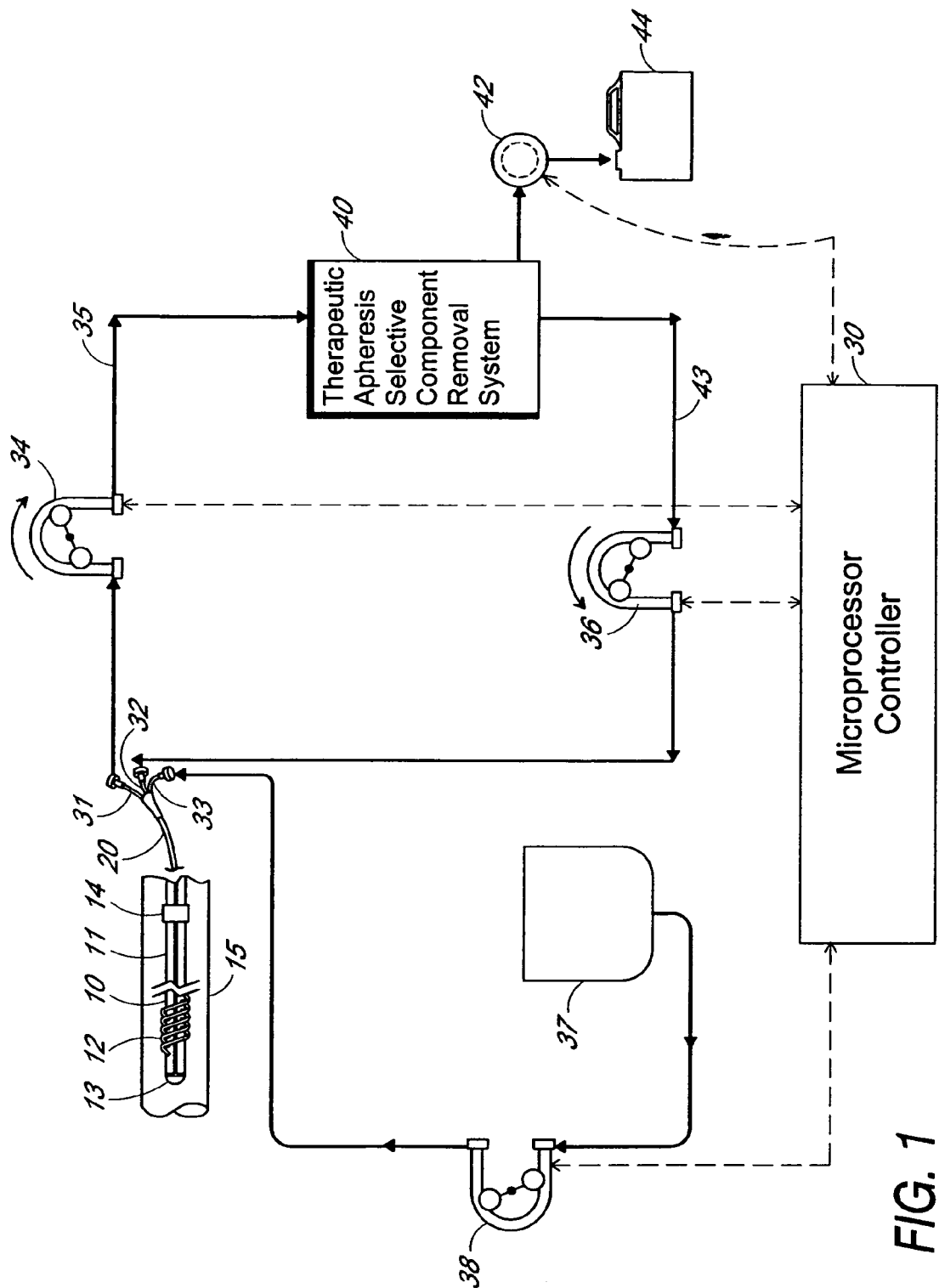
FIG. 1 is a schematic illustration of a preferred embodiment of apparatus for carrying out therapeutic apheresis.
Figure 4:
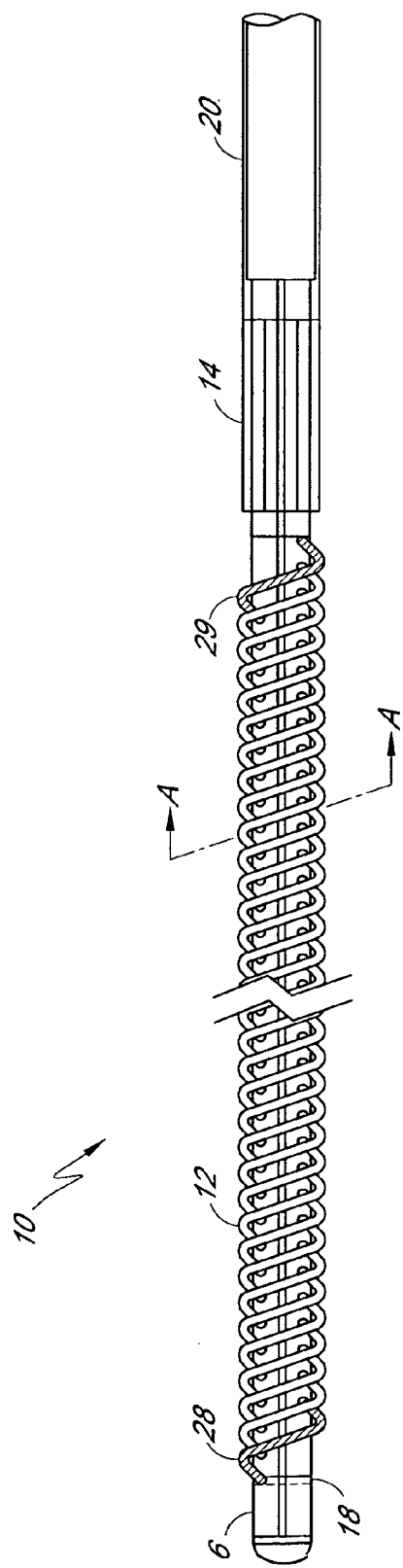
FIG. 4 is a top view of a preferred embodiment of a filter device shown in FIG. 1 for separating plasma from blood in-vivo having a pair of elongated substantially parallel hollow tubes joined together along their length, showing distal and proximal end segments.
Figure 6:
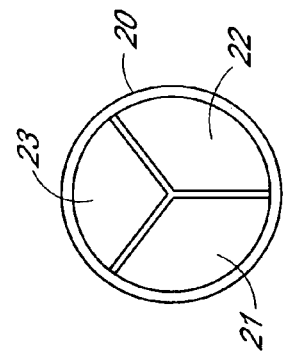
FIG. 6 is a sectional view of a triple lumen catheter of the apparatus shown in FIG. 1 illustrating the catheter interior.
Figure 5:
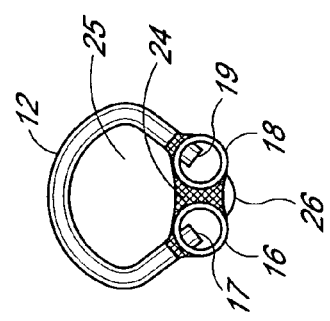
FIG. 5 is an enlarged sectional view of the filter device of FIG. 3 along the lines A-A showing a single elongated hollow fiber secured to the hollow tubes.

The preferred embodiment of an apparatus for carrying out therapeutic apheresis according to the invention schematically illustrated in FIG. 1 includes a filter device 10, a triple lumen catheter 20, a therapeutic apheresis selective component removal apparatus 40, a fluid control assembly including tubing and pumps, and a microprocessor/controller 30. The filter device 10, which will be described in more detail hereinafter, is implantable in the vasculature of a patient or animal in which in-vivo plasma separation is to be carried out. Veins suitable for implanting the filter include the superior or inferior vena cava or the subclavian vein. In the drawing, the filter device 10 is shown implanted in the inferior vena cava 15. A triple lumen catheter 20 is secured to the proximal end 11 of the filter with header 14. Triple lumen catheter 20 is in fluid communication with the interior of the filter device with the three catheter lumens connected to tubing for directing outgoing plasma, return plasma, and backflush fluid. Referring also to FIGS. 4-6, plasma separated from whole blood through the microporous fibers 12 of the filter device are directed through access lumen 21 and first tubing 31 to selective component apparatus 40. Plasma is separated from whole blood within the blood vessel in which the filter device is inserted using trans-membrane pressure (TMP) supplied by access pump or first pump 34, a positive displacement volumetric pump that operates to regulate pressure and control trans-membrane pressure and plasma volume removal rate.

Plasma from the filter device is pumped to the therapeutic apheresis selective component removal apparatus 40 for selectively removing disease-related components such as toxins, antibodies, proteins, pathogens including bacteria, virus, etc., and other disease-related substances desired to be removed. Plasma components and solutes removed from the treated plasma are directed to a container 44. An effluent pump 42 is optional and may be advantageously used for assisting in controlling the rate of disease components removed by providing controlled trans-membrane pressure across filter membranes of the selective component removal apparatus. Plasma is returned to the patient via tubing 43 at a rate controlled by pump 36. The tubing 43 is in fluid communication with plasma return tube 32 which is connected to plasma return lumen 22 of triple lumen catheter 20 (FIG. 5).

Examples of selective component removal apparatus used for therapeutic apheresis include plasma exchange components, centrifugal or membrane-separation filters, such as disclosed in U.S. Pat. No. 5,605,627, cascade or multiple filtration membranes and columns, cartridges having components for absorbing (adsorbing) specific disease-related components, and activated charcoal cartridges. Other examples of useful selective component removal components include specialized columns utilizing materials such as cross-linked polyvinyl alcohol gel beads or microporous cellulose beads for removing specific amino acid ligands and antibodies. Further examples of selective component removal apparatus are chemical process systems for specialized uses such as heparin precipitation, plasma cyrofiltration, and salt-amino acid co-precipitation, and the like. Chemical process apparatus for effectively neutralizing disease related components in the plasma may also be used. These and other selective component removal apparatus and technologies are described in Therapeutic Apheresis, Official Journal of the International Society for Apheresis, Vol. 1-6, Blackwell Science Inc., "Present Status of Apherisis Technologies", e.g. Vol. 1, No. 2, May, 1997, pp. 135-146, the descriptions of which are incorporated herein by reference. Combinations of two or more of any of the aforesaid apparatus may also be used.

Figure 2:
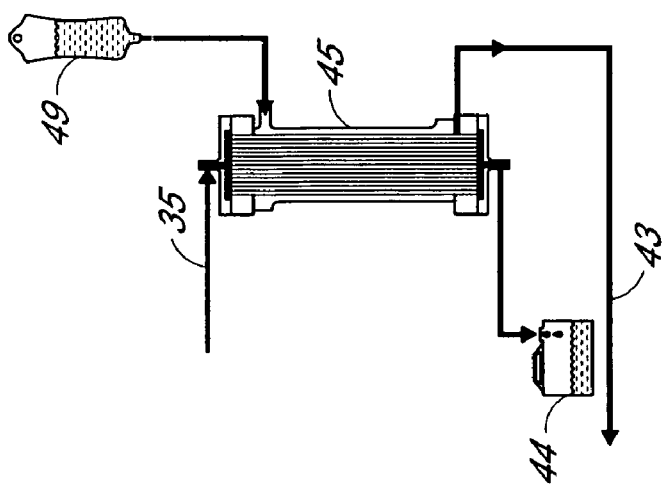
FIG. 2 schematically illustrates one embodiment of therapeutic apheresis apparatus using plasma exchange.

FIG. 2 illustrates a plasma exchange apparatus 45 for separating plasma components and for delivering fresh plasma from supply source 49. The plasma exchange rate may be selected as a function of the plasma removal rate by proportioning the rate of operation of access pump 34 to effluent pump 42, as shown in FIG. 1.

Figure 3:
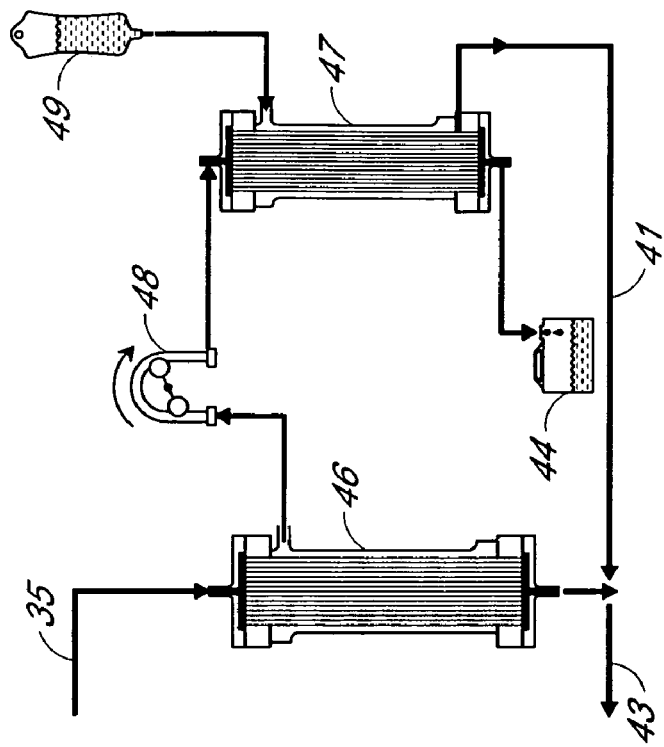
FIG. 3 schematically illustrates a therapeutic apheresis apparatus embodiment using double, cascade filtration.

FIG. 3 schematically illustrates an example of selective component removal apparatus showing a cascade filter comprising a first stage filter 46 and a second stage filter 47. A pump 48 is used for directing fluid plasma from the first stage filter to the second stage filter. A source of make-up plasma liquid 49 may be used, if desired, for introducing substitution fluids such as fresh plasma which is combined with the treated plasma to be returned to the patient via tubing 41 and 43. Container 44 receives and collects discarded plasma fluid containing disease-related components, such as toxins, etc. as previously described. In a single stage treatment apparatus, the use of a make-up plasma liquid is also optional as is effluent pump 42 shown in FIG. 1 and cooperating with selective component removal apparatus 40 for directing fluid and components to be discarded. Again, following treatment in selective component removal apparatus 40, plasma is returned to the patient via piping 43 and positive displacement pump 36 to plasma return tube 32 which is in fluid communication with plasma return lumen 22 of triple lumen catheter 20 (see FIG. 6).

An apparatus using cartridges or columns for absorbing or adsorbing disease-related components may also be used for treating separated plasma. Such apparatus may be configured like or similar to that illustrated in FIGS. 2 and 3 in which the columns shown incorporate absorbing or adsorbing filters comprising materials capable of absorbing selected disease-related components such as discussed herein. Again, such an apparatus may include a source of fresh plasma to be directed to the patient, if desired.

The preferred apparatus shown in FIG. 1 includes backflush fluid reservoir 37, backflush pump 38 and backflush tube 33 communicating with a backflush lumen of the triple lumen catheter. Such backflush components and method are disclosed in U.S. Pat. No. 6,659,973, the descriptions of which are incorporated herein by reference. Backflush pump 38 is selectively and periodically operated to provide backflush fluid flow for substantially cleansing the pores of the fiber membrane of the filter device. Such a backflush cycle is preferably operated at high trans-membrane pressure and low volume and at relatively short injection times for backflushing whereby the membrane pores are temporarily expanded and flushed to dislodge adhered proteins, thereby restoring pore integrity and density of the virtual filter area for improved performance after each backflush cycle.

Fluid control of plasma within the apparatus may be controlled using a microprocessor/controller operatively communicating with the positive displacement volumetric pumps for controlling trans-membrane pressure in the filter device and selective component removal apparatus, plasma removal rate, plasma return rate and backflush pressure and rate. Such fluid control and management may be selected, tailored or designed for slow, continuous acute fluid removal. For example, operation of the system may be used for controlling plasma extraction rate from blood to achieve removal of 1-2 L of plasma water over a 24-hour period. The fluid control assembly may also include volume sensors, pressure sensors, blood leak detectors and air detectors connected to the piping and reservoirs as desired. As illustrated in FIG. 1, the microprocessor/controller 30 is operatively connected to the pumps. Similarly, the microprocessor/controller operates for controlling backflush pump 38 and plasma is returned at a selected rate by controlling pump 36. The microprocessor/controller may be programmed for flow rates designed to a the prescribed patient therapy.

In a preferred embodiment of the filter device 10 illustrated in FIGS. 1, 4 and 5, a pair of elongated hollow tubes are joined side-by-side lengthwise to form the core of the filter device. The two elongated hollow core tubes 16 and 18 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material 24, adhesive composition, etc., for example, a UV curable adhesive applied along the length between the two tubes. The length and diameter of the filter device may be selected to accommodate the vessel or vein in which it is to be implanted. Accordingly, the diameter and length of the one or more elongated hollow tubes forming the central core of the filter device are selected. A suitable tube length is between about 15 cm and about 25 cm, and preferably between about 18 cm and about 22 cm. Where a pair of core tubes is used as shown in the preferred embodiment, an outer diameter of each tube of between about 1 mm and about 3 mm is suitable. A detectable marker component 26, e.g., a radio opaque material, may also be bonded to the device, for example, in bonding material 24 extending along the length of the tubes to assist in implanting and/or monitoring the device during insertion, use and removal.

Effective plasma separation is also a function of fiber length. Thus, the length of the individual hollow fibers is preferably less than about 5 mm and preferably between about 1 mm an about 4 mm. Moreover, fiber orientation relative to blood flow within the vessel is also of significant importance. Preferably, the fibers are aligned so that the longitudinal fiber axis is between about 45° and about 90° relative to the direction of blood flow. The filtration performance of a filter device to separate plasma from whole blood in-vivo is also a function of the filter surface of the exposed fibers whereby consideration is given to use larger diameter fibers and to maximize the number of fibers. It is desirable to use as many individual fibers along the hollow core tubes of the filter device as is practical while maintaining separation of the individual fibers to provide for fluid flow therebetween, and to maximize the amount of outer fiber surface exposed to blood flowing along the length of the filter device. Moreover, the fibers are secured along the length of the hollow tubes in such a manner as to form a fluid flow space between the fibers and the tubes. The length of the filter device as well as the overall cross-sectional dimension are tailored or dictated by the blood vessel in which the device is to be used so as to avoid substantial interference with blood flow through the vessel while at the same time be efficient to achieve the intended flow rate of separated plasma.

Preferably, the ends of each of the fibers are offset longitudinally relative to one another. Referring to FIGS. 4 and 5, elongated hollow fiber 12 has a first end 17 secured in first elongated hollow tube 16 and second end 19 secured in second hollow tube 18. In the specific device illustrated, the longitudinal spacing between the first and second ends of each fiber is a three-hole or three-fiber offset, e.g., about 0.5 cm. However, with intervals between the adjacent fiber ends of between about 0.1 cm and about 1.0 cm, offsets between first and second fiber ends may be between about 0.3 cm and about 3.0 cm, by way of example. With such offsets between first and second fiber ends, a straight line extending between the ends of a fiber forms an acute angle with an elongated axis of either or both of the elongated hollow tubes, and whereby the fibers also extend lengthwise between their ends along an angle other than 90° relative to the axes of the elongated hollow tubes. The acute angle preferably is between about 45° and about 85°. However, other fiber angles including 90° are not precluded and may be used where desired. Such fiber angles provide desirable fiber orientation relative to blood flow as previously described. Other filter device embodiments which may be used are disclosed in U.S. Pat. No. 6,899,692, the descriptions of which are incorporated herein by reference.

Conventional hollow fibers or filter membranes such as those used in conventional dialysate filter devices are unable to successfully perform in-vivo, intravascular plasma separation, becoming clogged within a very short period of time, e.g., minutes, as proteinaceous materials, blood platelets, and other components rapidly occlude the membrane pores. Conventional dialysate filter membranes have little structural strength which, although acceptable in an encapsulated dialysate filter environment external to the body, are not suitable for intravascular use. Moreover, conventional dialysate hollow fiber membrane filters do not perform satisfactorily in-vivo because of the relatively high flow rate of blood at the exterior fiber surface and relatively low lumen pressure as compared to dialysate filter apparatus conditions in which plasma separation is carried out at relatively low flow rates and high trans-membrane pressures. For example, typical in-vivo blood flow within a vena cava is about 2.5 L per minute, while blood flow through typical dialysate filter apparatus is nearly stagnant, e.g., about 0.42 ml per minute per fiber. Intravascular trans-membrane pressure is typically about 50 mm Hg or less, as compared to 100-300 mm Hg used in extracorporeal dialysate filters.

Figure 7:
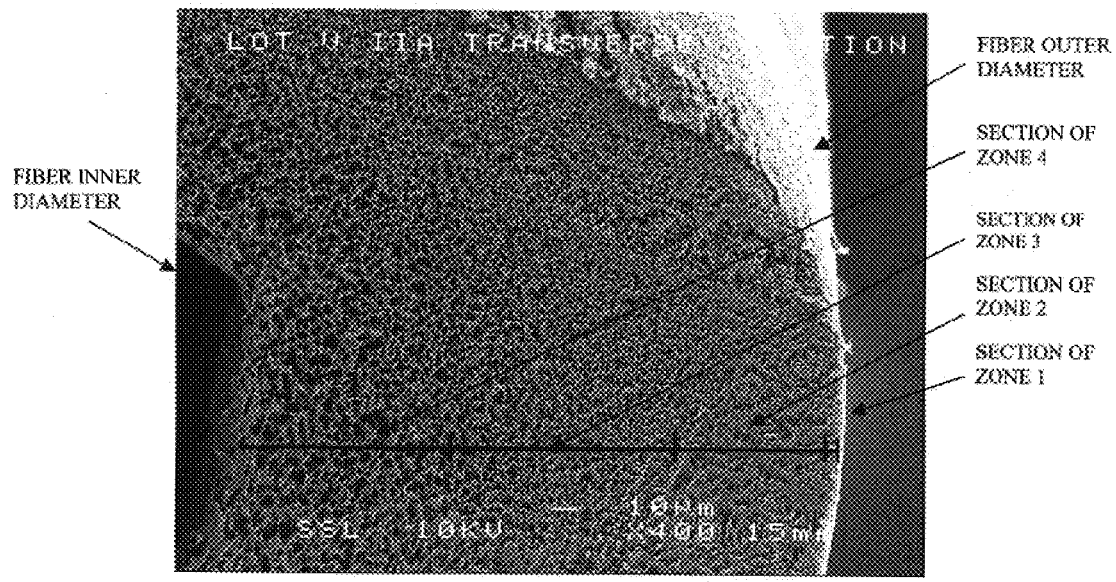
FIG. 7 is a scanning electron microscopy (SEM) image of a cross-section of a preferred elongated hollow fiber used in a filter device shown in FIG. 3 at 400× magnification.

The preferred elongated hollow microporous fibers used in the filter device described herein are the asymmetrical wall fibers disclosed in U.S. Pat. No. 6,802,820, the descriptions of which are incorporated herein by reference. The fiber wall structure of the elongated microporous fibers is asymmetrical between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIG. 7 showing a scanning electron microscopy (SEM) image of a cross-section of the fiber at 400× magnification. It will be observed that the structure of the fiber from the outer surface to the lumen is a continuous change in mass density whereby the pore size gradually changes between these fiber wall surfaces. The fiber walls are also characterized by a substantially uniform wall thickness between the inner and outer wall surfaces and have substantially no macrovoids other than the pores, as shown. It is convenient to describe the continuum of different mass density as sections or zones of the wall area having an average nominal pore size or average pore diameter, each zone having a different average nominal pore size. Thus, the walls may be characterized by two or more zones, for example 2, 3, or 4 or more mass density zones. The hollow fiber shown in FIG. 7 is also shown and described in the aforesaid U.S. Pat. No. 6,802,820. In the fibers, the outer surface of the membrane, zone 1, has the highest mass density characterized by smaller average pore diameters. The outer zone forms the fiber interface with the permeate blood flow by determining filtration characteristics including the composition and components of separated plasma and controlling fiber membrane performance. Thus, zone 1 is the principle filtration portion of the fiber wall for controlling the trans-membrane flux (TMF) for excluding even the smallest cells in the blood, the platelets, having a diameter of about 1 μm. Nominal average pore diameters in zone 1 are between about 0.3 μm and about 1 μm, and preferably range from about 0.4 μm to about 0.8 μm. A preferred filtration sizing has a cutoff of about 0.6 μm to about 0.8 μm. Zones 2 and 3 are designed to decrease the flow path tortuosity and maintain the structural integrity required of the fiber exposed to physical conditions within the body. Pore size distribution in these zones ranges gradually from about 0.8 μm to about 1.2 μm and from about 1.2 μm to about 2.0 μm. Zone 2, having some flux-controlling pores, is principally to provide structural strength to the fiber as well as acting as a conduit for exudate flow to zone 3, also providing structure and enlarged pores for reducing the hydraulic resistance and providing a fluid conduit to the fiber lumen. The interior zones have little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 μm and about 60 μm, and preferably between about 2 μm and about 6 μm. A typical fiber as shown has an OD of about 650 μm, an ID of about 250 μm and a wall thickness of about 250 μm. However, such dimensions are by way of example only. Again, such fibers are more fully described in U.S. Pat. No. 6,802,971.

The elongated microporous fibers used in the filter device may be produced using biocompatible polymers including those produced from polyurethane, polypropylene, polysulfone (polyethersulfone), polycarbonate, nylon, polyimide, as well as other synthetic resins known to those skilled in the art. A preferred polymer is polysulfone, and more preferably a polyethersulfone/polyethylene oxide copolymer with a polyethylene glycol solvent or a polysulfone modified with polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. Specific methods for producing the aforesaid polymers and fibers are known to those skilled in the art and disclosed, for example, in PCT Publication WO 90/04609.

The advantages which may be accrued by using the therapeutic apheresis methods and apparatus described above include elimination of the disadvantages of the removal of whole blood from the body and subsequent ex-vivo plasma separation as previously described. In-vivo plasma separation permits continuous real time therapy in most applications with resultant improvement in effectiveness, and in many applications would result in the ability to perform the therapy in a home setting or ambulatory mode which could be a major improvement in patient lifestyle as well as economy for the medical care system. Moreover, the use of the methods and apparatus described herein would increase the capacity of most caregiver organizations which are now limited by patient load capacity including the number of centrifuge machines available in the facility.

Examples of diseases and disorders for which therapeutic apheresis may be used and the pathogenic substances removed using the methods and apparatus of the invention include those listed in Table 1, and described in *Therapeutic Apherisis*, Vol. 1, No. 2, 1997. The list is not intended to be exhaustive, and other diseases and substances may also be treated. Moreover, the methods and apparatus described herein may also be used in drug treatment, for example in drug overdose cases, where one or more toxic substances in the blood stream may be removed using the aforesaid methods and apparatus. These as well as others advantages will be evident to those skilled in the art.

TABLE 1

Disorders for which therapeutic plasmapheresis has been used and the pathogenic substances removed

| | Classification | | |
|---|---|---|---|
| | I. Abnormal protein-related disease | II. Autoimmune antibody-related disease | III. Immune complex-related disease |
| Collagen and rheumatological diseases | Raynaud's disease: Cryoglobulin macroglobulin | SLE: anti-DNA Ab, ANA, (IgG, M, A), anti-Sm Ab, anti-Ku Ab; anti-PCNA Ab | SLE |
| | RA: Cryoglobulin | RA: RP (IgM), anti-RANA Ab | RA |
| | | PSS: anti-nonhistone nuclear Ab | PSS |
| | | Scleroderma: anti-Og (Scl-70) Ab, (70,000) | Scleroderma |
| | | MCTD: anti-U, mRNP Ab, ANA, anti-Sip Ab, ENA, RF | |
| | | CREST syndrome: anti-centromere Ab | |
| | | Sjögren's syndrome: anti-SSA Ab, anti-mitochondria Ab, anti-SSBAb (l.aAb, HaAb), ENA, ANA | |
| | PN: Cryoglobulin | Overlap syndrome (PSS and PM): anti-Ku Ab | |
| | Macroglobulin | PN: RF | PN (11BsAg Ab immune complexes) |
| Neurological diseases | MG: Cryoglobulin | MG: anti-Ach R Ab, anti-SM Ab (IgG 1, 2, 3) anti-skeletal muscle Ab | |
| | | MS: anti-myelin Ab | |
| | | GBS: anti-myelin Ab, anti-SP-B8 Ab | GBS |
| | Polyneuropathy: Cryoglobulin | PM and DM: anti-Ju 1 (Ab, anti-PM-Scl Ab) | |
| | Macroglobulin | Polyradiculoneuropathy: anti-SP-B Ab | |
| Liver diseases | Pulminant hepatitis: Protein-bound toxins | Chronic active hepatitis: anti-mitochondrial Ab | |
| | Hepatic failure: Protein-bound toxins | | |
| | PBC: Protein-bound toxins | PBC: anti-mitochondrial Ab | |
| Hematological diseases | Paraproteinemia: Paraprotein | ITP: anti-platelet Ab (IgG) | |
| | Macroglobulinemia: Macroglobulin (hyperviscosity syndrome) (IgM) (900,000) | TTP: anti-platelet Ab (IgG) | TTP |
| | | Autoimmune hemophilia A: anti-factor VIII Ab | Schönlein-Henoch purpura |

TABLE 1-continued

Disorders for which therapeutic plasmapheresis has been used and the pathogenic substances removed

| | Classification | | |
|---|---|---|---|
| | I. Abnormal protein-related disease | II. Autoimmune antibody-related disease | III. Immune complex-related disease |
| | | Cryoglobulinemia: Cryoglobulin | Preparation for ABO incompatible marrow transplantation: anti-A or B Ab<br>RH incompatibility: anti-Rh Ab<br>Autoimmune hemolytic anemia: anti-red cell Ab, cold-hemolysin (IgG), cold-hemaglutinin (IgM)<br>Pernicious anemia: intrinsic factor Ab (IgG, M, A) | |
| Renal diseases | AIDS: Suppressor factors? | AIDS: anti-lymphocyte Ab<br>Anti-glomerular basement membrane GEM mediated glomerulonephritis: anti-GDM glomerulonephritis (IgG, M, A)<br>Goodpasture's syndrome: anti-glomerular basement membrane Ab<br>Rejection of kidney transplantation: anti-IILA Ab | AIDS<br>Immune complex glomerulonephritis<br><br><br>Rejection of kidney transplant |
| Malignant diseases | Cancer: CA19-9 (820,000), $\alpha_2$ MG (820,000), CEA (200,000), AFP (70,000), IAP (57,000), etc.<br>Multiple myeloma: M-protein (IgG, M, A, E) | Cancer: tumor-specific antibody | Cancer |
| Others | Hyperlipidemia: LDL, VLDL<br>Familial hypercholesterolemia | DM I-B type: anti-insulin receptor Ab<br>Insulin autoimmune syndrome: anti-insulin Ab (IgG, A)<br>Asthma: IgE<br>Urticaria: IgE | |
| | Toxins | Ulcerative colitis: anti-colonic lipopolysaccharide | |
| | Poisons | Basedow's diseases (Graves' disease): LATS (IgG)<br>Autoimmune thryoiditis: anti-microsomal Ab<br>Hoshimoto's disease: anti-thyroglobulin Ab<br>Addison's disease: anti-adrenal Ab (IgG)<br>Autoimmune chronic atrophic gastritis: parietal cell Ab (IgG, M, A)<br>Chronic ulcerative colitis: anti-colonic epithelial cell Ab<br>Pemphigus: anti-epidermal cell membrane glycoproteins Ab | |

SLE, systemic lupus erythematosus; RA, rheumatoid arthritis; PSS, progressive systemic sclerosis; MCTD, mixed connective tissue disease; PN, periarteritis nodosa; MG, myasthenia gravis; MS, multiple sclerosis; GBS, Guillain-Barré syndrome; PM and DMS, polymyositis and dermatomyositis; PBC, primary biliary cirrhosis; ITP, idiopathic thrombocytopenia purpura; TTP, thrombotic thrombocytopenic purpura; DM, diabetes mellitus; AIDS, acquired immunodeficiency syndrome; ENA, anti-extractablenuclear antibody; RNP, ribonucleoprotein; ANA, anti-nuclear Ab: HLA, human leukocyte antigen; LATS, long-acting, thyroid stimulator; Ab, antibody; RF, rheumatoid factor; RANA, rheumatoid-associated nuclear antigen.

What is claimed is:

1. Apparatus for carrying out therapeutic apheresis comprising:
   an implantable filter device comprising a plurality of elongated hollow tubes and a plurality of elongated microporous fibers capable of separating plasma from whole blood in-vivo, each fiber having an interior lumen extending along the length thereof and having a first and second end secured to different ones of said elongated hollow tubes wherein the interior lumen of each of the fibers communicates with the interior of two of said elongated hollow tubes;
   a triple lumen catheter secured to the proximal end of the filter device having one or more lumens in fluid communication with the interior of said elongated hollow tubes and a plasma return lumen; and
   therapeutic apheresis apparatus for removing and/or separating selected disease-related components from the separated plasma and tubing for directing plasma between said catheter and the selective component removal apparatus.

2. Apparatus of claim 1 wherein said triple lumen catheter comprises a first lumen and a second lumen in fluid communication with the interior of said elongated hollow tubes and a third lumen comprising said plasma return lumen.

3. Apparatus of claim 1 wherein said therapeutic apheresis apparatus comprises a plasma exchange assembly.

4. Apparatus of claim 1 wherein said therapeutic apheresis apparatus comprises a multiple stage filtration assembly.

5. Apparatus of claim 1 wherein said therapeutic apheresis apparatus comprises one or more columns or cartridges containing materials for absorbing disease-related components passing therethrough.

6. Apparatus of claim 1 wherein said selective component removal apparatus comprises one or more reactors containing compositions for reacting with disease-related components in the plasma.

7. Apparatus of claim 1 including:
   a fluid control assembly comprising first tubing in fluid communication with said first lumen of said catheter and a first fluid pump cooperating therewith for directing plasma from said filter device, second tubing in fluid communication with said second lumen of said catheter and a second pump cooperating therewith for directing backflush fluid into said filter device, and third tubing in fluid communication with said third lumen of said catheter for directing plasma from the therapeutic apheresis apparatus to a patient; and control apparatus operatively communicating with said first and second pumps for controlling the operation thereof, respectively.

8. Apparatus of claim 7 including a third pump cooperating with said third tubing and in control connection with said control apparatus.

9. Apparatus of claim 7 including a source of backflush fluid cooperating with said second tubing.

10. Apparatus of claim 7 wherein said control apparatus comprises a microprocessor-controller including software programmed for operating one or more of said pumps.

11. Apparatus of claim 8 wherein said control apparatus comprises a microprocessor-controller including software programmed for operating one or more of said pumps.

12. Apparatus of claim 9 wherein said control apparatus comprises a microprocessor-controller including software programmed for operating one or more of said pumps.

13. Apparatus of claim 1 wherein said filter device comprises first and second elongated hollow tubes extending substantially parallel along the length thereof, and wherein a first end of each of said elongated microporous fibers is secured to a first hollow tube and a second end of each of said fibers is secured to a second hollow tube whereby the interior fiber lumen of each fiber communicates with the interior of a first and a second elongated hollow tube.

14. Apparatus of claim 13 wherein the first elongated hollow tube extends along a first axis and the second elongated hollow tube extends along a second axis substantially parallel with said first axis, and wherein the first ends of said elongated microporous fibers are secured to said first elongated hollow tube along a generally straight first row, and the second ends of said elongated microporous fibers are secured to said second elongated hollow tube along a generally straight second row substantially parallel with said first row.

15. Apparatus of claim 14 wherein each of said fibers are generally bowed along its length between said first and second ends to form an arch spaced apart from said elongated hollow tubes and forming a passageway therebetween.

16. Apparatus of claim 13 wherein the first and second ends of said elongated microporous fibers are secured to said first and second elongated hollow tubes, respectively, at substantially regular intervals.

17. Apparatus of claim 14 wherein said regular intervals are between about 0.1 cm and about 1.0 cm.

18. Apparatus of claim 1 wherein the length of each of said elongated microporous fibers is between about 1 cm and about 4 cm.

19. Apparatus of claim 13 wherein the length of each of said elongated microporous fibers is between about 1 cm and about 4 cm.

20. Apparatus of claim 14 wherein the length of each of said elongated microporous fibers is between about 1 cm and about 4 cm.

21. Apparatus of claim 14 wherein the first end of each elongated microporous fiber is offset longitudinally from the second end of each said fiber along the length of said elongated hollow tubes whereby a straight line extending through the first and second end of a fiber forms an acute angle with one of said axes.

22. Apparatus of claim 21 wherein the length of each elongated hollow tube is between about 10 cm and about 25 cm, wherein the length of each elongated microporous fiber is between about 1 mm and about 4 mm, wherein the space between adjacent fibers is between about 0.1 cm and about 0.3 cm, and wherein said acute angle is between about 45° and about 85°.

23. Apparatus of claim 1 wherein the fiber wall morphology of the elongated microporous fibers is asymmetrical between the inner wall surface extending along the interior fiber lumen and the outer wall surface, said fiber wall having a higher mass density zone adjacent to the outer wall surface and a lower mass density zone adjacent to the inner wall surface, said higher mass density zone having a smaller average nominal pore size than the average nominal pore size of the lower mass density zone.

24. Apparatus of claim 23 wherein the fiber wall structure comprises a continuous change in mass density between the inner and outer surfaces of the fiber.

25. Apparatus of claim 7 including a container cooperating with said therapeutic apheresis apparatus for receiving effluent therefrom.

26. Apparatus of claim 25 including fourth tubing in fluid communication with said container and said therapeutic apheresis apparatus.

27. Apparatus of claim 26 including an effluent pump cooperating with said fourth tubing for pumping effluent from said therapeutic apheresis apparatus to said container.

28. Apparatus of claim 27 including control connection between said control apparatus and said effluent pump.

29. Apparatus of claim 28 wherein said control apparatus comprises a program for directing operation of said apparatus.

30. Apparatus of claim 28 wherein said control apparatus comprises a program for controlling operation of one or more of said pumps.

31. Apparatus of claim 28 wherein said control apparatus comprises a microprocessor-controller including a program for controlling operation of one or more of said pumps.

32. Apparatus of claim 23 having a lower mass density zone characterized by a nominal average pore diameter of between about 1 μm and about 60 μm.

33. Apparatus of claim 23 having a higher mass density zone characterized by a nominal average pore diameter of between about 0.3 μm and about 1 μm.

34. Apparatus of claim 32 having a higher mass density zone characterized by a nominal average pore diameter of between about 0.3 μm and about 1 μm.

35. Apparatus of claim 34 wherein the nominal average pore diameter in said lower mass density zone is between about 2 μm and about 6 μm.

36. Apparatus of claim 35 wherein the nominal average pore diameter in said higher mass density zone is between about 0.4 μm and about 0.8 μm.

37. Apparatus of claim 34 having one or more intermediate mass density zones having a nominal average pore diameter of between about 0.8 μm and about 2 μm.

38. Apparatus of claim 35 having two intermediate mass density zones, a first intermediate zone having a nominal average pore diameter of between about 0.8 μm and about 1.2 μm and a second intermediate zone having a nominal average pore diameter of between about 1.2 μm and about 2 μm.

39. Apparatus of claim 23 wherein said fibers comprise a polysulfone fiber.

40. Apparatus of claim 21 wherein the fiber wall structure comprises a continuous change in mass density from said outer wall surface to said inner wall surface and comprises a continuum of voids bounded by solid frames, said fiber wall having an asymmetrical pore size and asymmetrical mass density between said inner wall surface and the outer wall surface.

41. Apparatus of claim 40 wherein said fibers comprise a polysulfone fiber.

* * * * *